Figure 1:
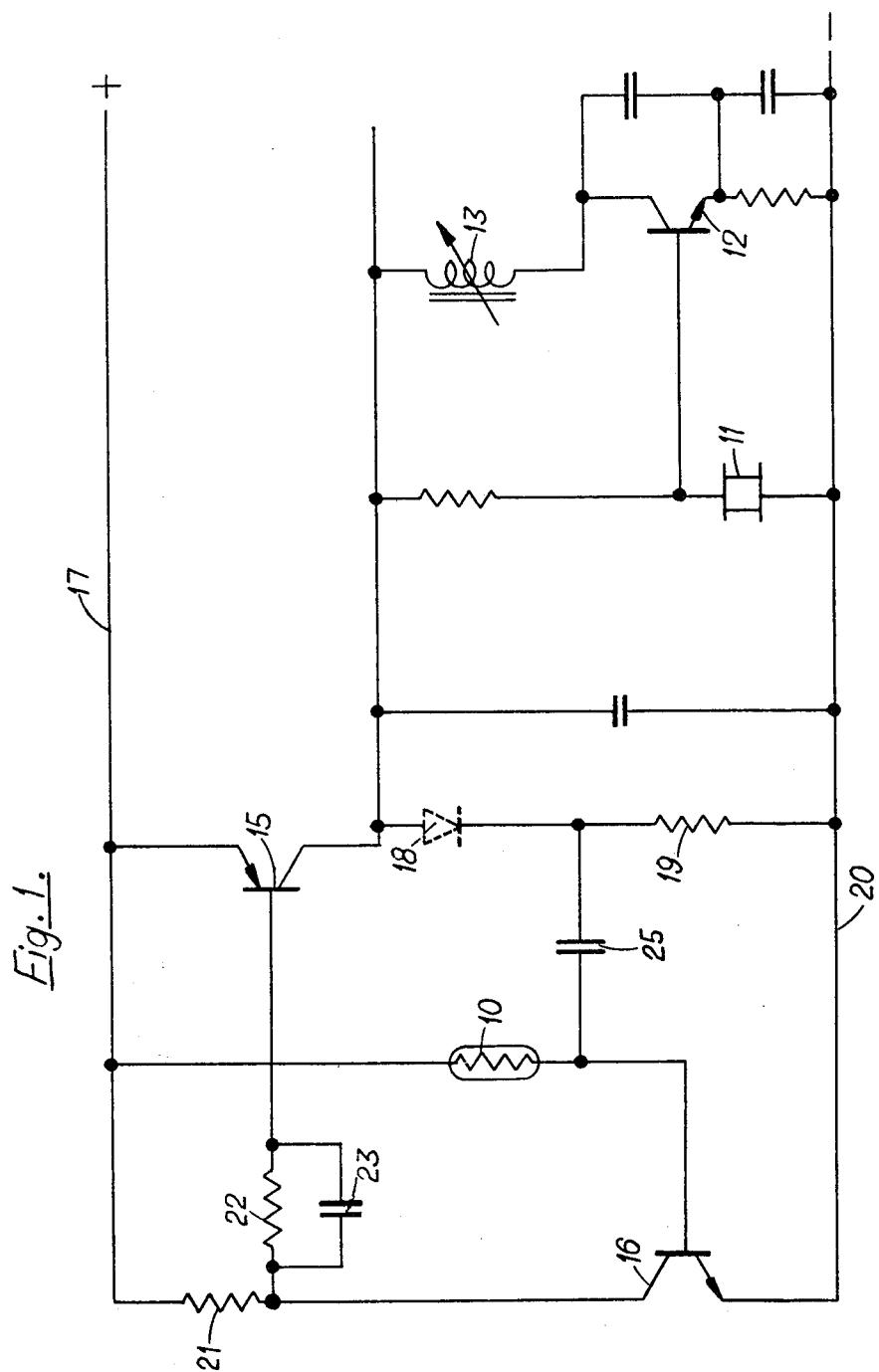

United States Patent [19]
Gallant et al.

[11] 3,953,803

[45] Apr. 27, 1976

[54] MEASURING SYSTEM

[75] Inventors: John Henry Gallant, Upminster; Michael Robert Thomas Johnson, South Ockendon, both of England

[73] Assignee: May & Baker Limited, Dagenham, England

[22] Filed: Dec. 28, 1973

[21] Appl. No.: 429,692

[30] Foreign Application Priority Data
Jan. 2, 1973 United Kingdom............... 00218/73

[52] U.S. Cl................................ 328/112; 307/234
[51] Int. Cl.²..................... H03K 5/18; H03K 5/20; H03K 9/08
[58] Field of Search............... 324/186, 78 D, 79 D; 307/234, 235 R; 328/111, 112, 117, 151

[56] References Cited
UNITED STATES PATENTS

| | | | |
|---|---|---|---|
| 3,116,458 | 12/1963 | Margopoulos | 328/151 X |
| 3,508,158 | 4/1970 | Marchese | 328/117 |
| 3,780,346 | 12/1973 | Gagnon | 317/5 |
| 3,790,881 | 2/1974 | Smith | 328/111 X |

*Primary Examiner*—John Zazworsky
*Attorney, Agent, or Firm*—Stevens, Davis, Miller & Mosher

[57] ABSTRACT

A measuring system in which a signal representative of the instantaneous value of a physical parameter being measured is utilized as a reference signal against which the next following signal is compared and so on. The system includes means for passing to an output, signals similar to, or within a predetermined limit of, the immediately preceding signals. A particular application of this measuring system is in the measurement of the temperature of living bodies wherein the changes in temperature are transmitted via a pulse width modulation telemetry system to a receiver incorporating the measuring system. By means of continually up-dating the reference signal it is possible to reject any signal which due to some reason such as radio interference is unacceptable because it varies too much from the previous reading.

9 Claims, 6 Drawing Figures

Note: The complete Convertor consists of 10 identical circuits as shown above

MEASURING SYSTEM

The present invention relates to a measuring system, for measuring a continuously variable parameter. The main object of the system is to prevent spurious signals representative of the parameter from being read or recorded.

According to one aspect of the present invention there is provided a measuring system comprising a signal processor including first memory means for storing a next following signal representative of the instantaneous value of a parameter being measured, second memory means for storing the previous signal representative of the instantaneous value of the parameter being measured, which serves as a reference signal, comparison means for comparing said reference signal with said next following signal, means for passing to an output a signal which is within a predetermined limit of the preceding signal and means for up-dating said second memory means by entering said next following signal into the second memory means, which signal acts as the next reference signal.

Using such a system should one instantaneous signal differ from its preceding reference signal, then it will be rejected. However, as the parameter changes, assuming a high rate of sampling, the next signal thereafter will be the same as the rejected signal which has become by then a reference signal so that a changing parameter can be measured. It will be appreciated, therefore, that the reference signal is continually being updated as it always comprises the immediately preceding reading. Should an instantaneous spurious signal occur, it itself will be rejected as a reading and the next signal will be rejected because it will not be the same as said spurious signal. However, the next subsequent correct signal will be recorded, because it should then be the same as its preceding reference signal.

The system according to the present invention has particular but not exclusive application in measuring biological changes, for example, changes in body temperature, pulse rate or respiratory rate. Further, the system may be adapted for use in the remote measurement of temperature, pulse rate or respiratory rate changes taken at a series of sampling points, such as different patients in a hospital ward and caged animals being used to test the effectiveness of new drugs under controlled laboratory conditions, and communicated to a central control point, for example, by a radio transmitter/receiver link. An advantage of using the measuring system in this manner is that it is possible for the people or animals to move freely within the confines of their environment whilst the measurements are being made, if necessary, continuously. As a result more accurate readings are obtained as compared with taking spot measurements using, for example, thermometers because in the case of handling animals it has been found that various temporary changes take place, for example an initial lowering of the skin temperature.

In order for a remote measuring system to be effective it is necessary that it should be able to discriminate between a useful signal and a signal which is not useful because, for example, it is distorted by extraneous electrical noise and/or the transmitter section is malfunctioning.

In an embodiment of the present invention there is provided a pulse width discriminator adapted to receive a pulse-like signal and to generate an output signal if the width of the received signal is within a predetermined limit, and a signal processor responsive to the output signal for determining the duration of the period of time between adjacent pulses of the received signal, which period is related to the value of the physical variable being measured, and also whether the determined period is such as to represent an acceptable signal which can subsequently be utilized, by comparing a signal representative of the period with the immediately preceding signal representative of the period.

The signal processor suitably may comprise a clock pulse generator, a first counter and a second counter both coupled to receive clock pulses from the clock pulse generator, in response to the output signal from the pulse width discriminator. The second counter can include a store for storing the immediately preceding count held in the first counter and is arranged to subtract from the stored count the received clock pulses. The signal processor may further comprise means for determining whether the difference between the previous count and the newly received count is within a predetermined limit and, if so, to transfer the count in the first counter to an output of the signal processor. Said means may also be arranged to transfer the count recorded in the first counter into the second counter irrespective of whether a signal appears at the output of the signal processor. A signal converter may be connected to the output of the signal processor for converting the output therefrom into a signal representative of the physical parameter being measured. Conveniently, the first and second counters may comprise binary counters. The means for determining whether the difference between the previous count and the newly received count is within a predetermined limit, the means for transferring the count in the first counter to an output of the signal processor and the means for transferring the count recorded in the first counter into the second counter irrespective of whether the signal appears at the output of the signal processor may all comprise suitably connected logic means including, for example, NAND and NOR gates, monostable circuits and gated memory circuits.

The pulse width discriminator may conveniently comprise two counters having different maximum counts, the difference between the two maximum counts being such as to form a window, the width of which corresponds to the predetermined limits within which the received pulse-like signal can vary without it being rejected. If, for example, one counter counted up to ten and the second counter up to sixteen, then the window would represent six counts, namely the difference between 10 and 16.

If the measuring system is adapted for multi-channel use then it may further comprise a channel selector so connected that the change in a physical parameter at a plurality of sampling points or stations can be determined by indexing the channel selector in turn through the various sampling points. In the case of a channel being temporarily or permanently defective, the signal processor is linked to the channel selector so that if an unacceptable reading is obtained after the sampling point has been interrogated a predetermined number of times in succession then the channel selector will be indexed onto the next channel. The channel selector may include an alarm signalling device which is actuated in the event of a particular channel appearing to be permanently defective which is indicated by a channel still producing an unacceptable signal after the channel has been sampled a predetermined number of times.

The measuring system may be adapted for use with a plurality of radio transmitters having their own distinctive carrier frequencies, in which case the measuring system further comprises a radio receiver which is controllable by the channel selector to receive and demodulate the signals from the selected transmitter.

Figure 2:
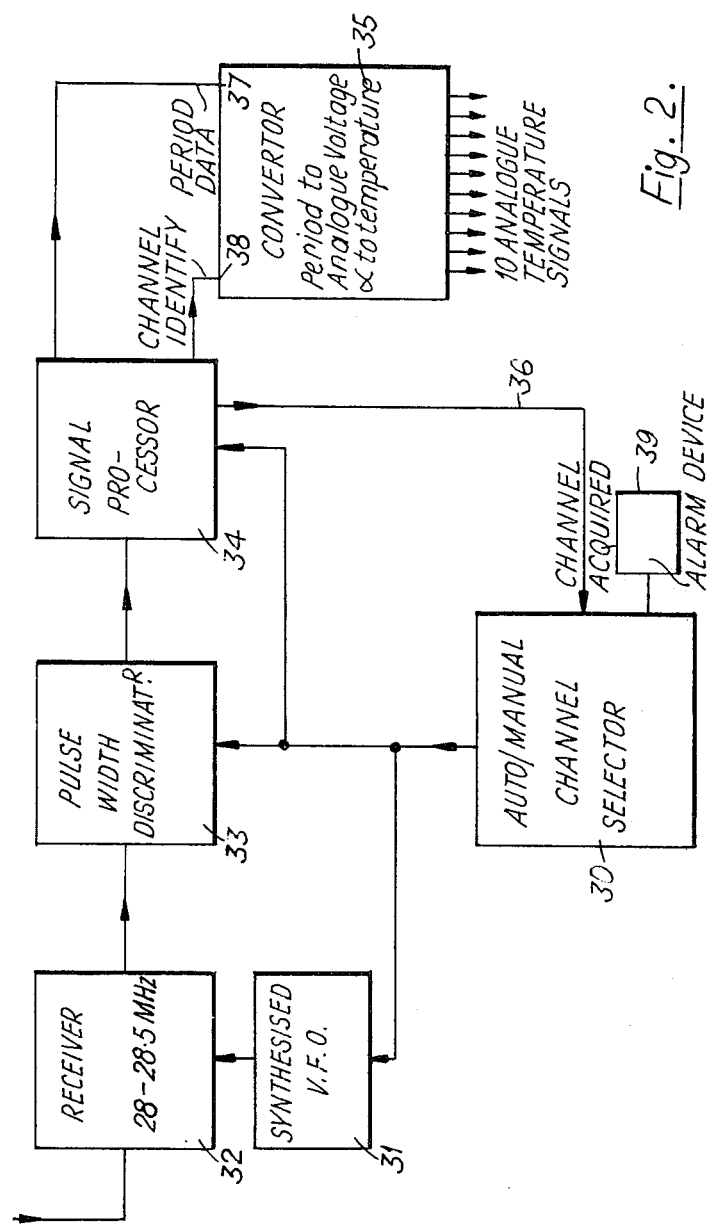
Figure 3:
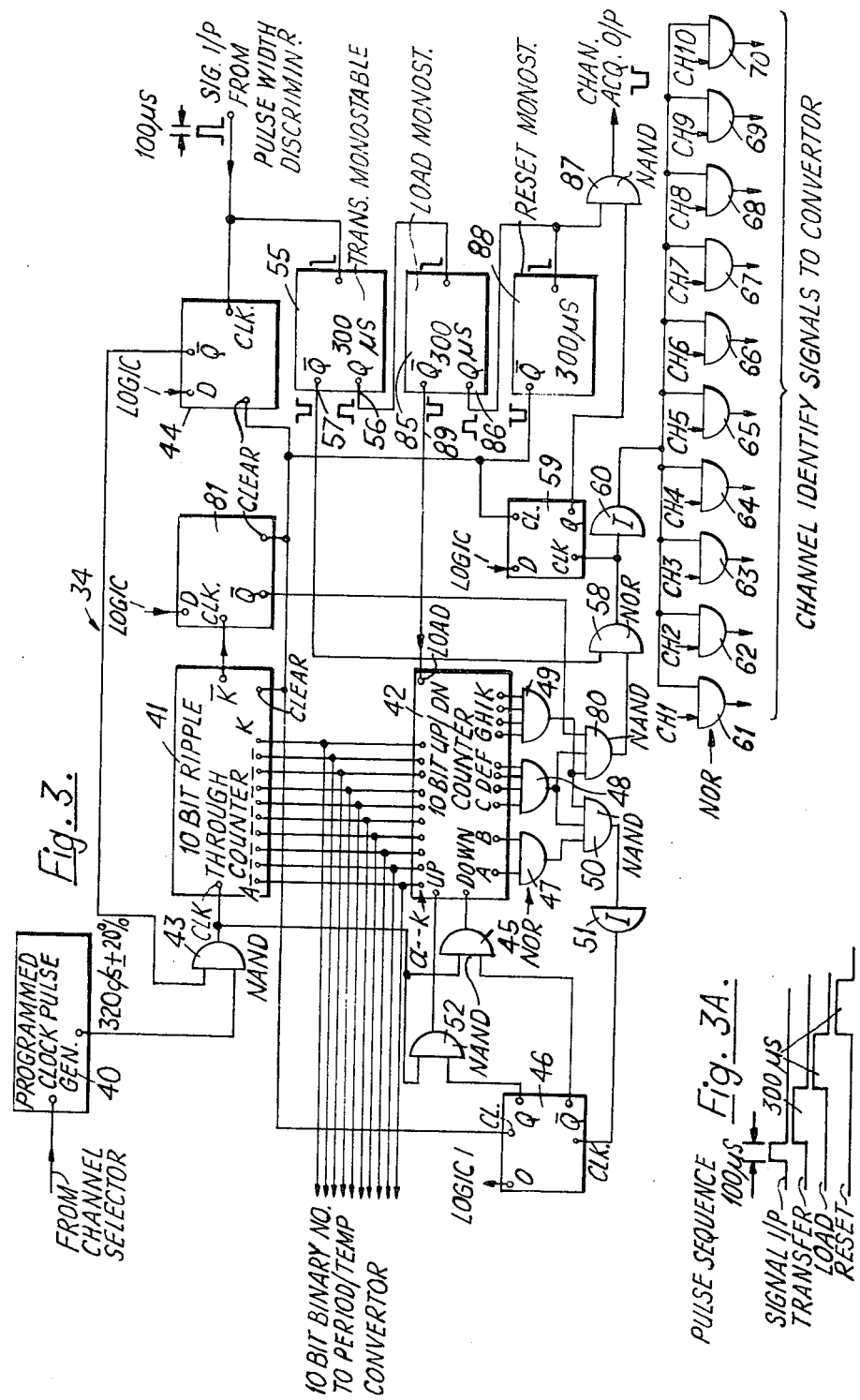
Figure 4:
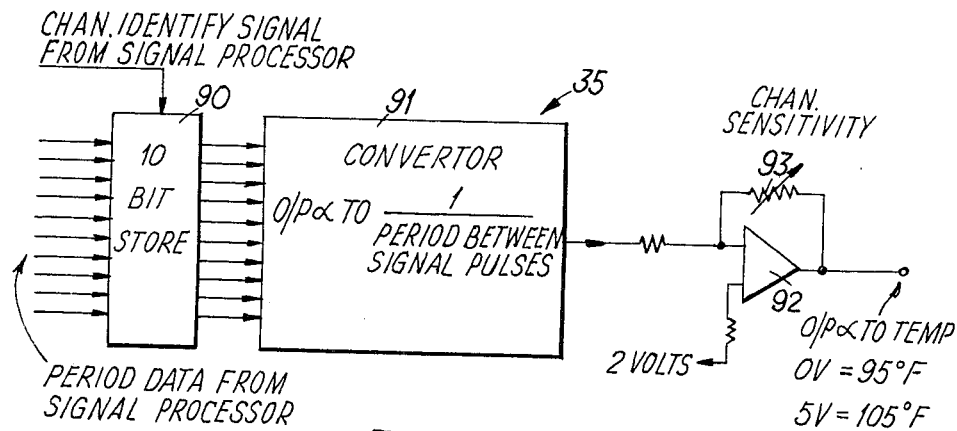
Figure 5:
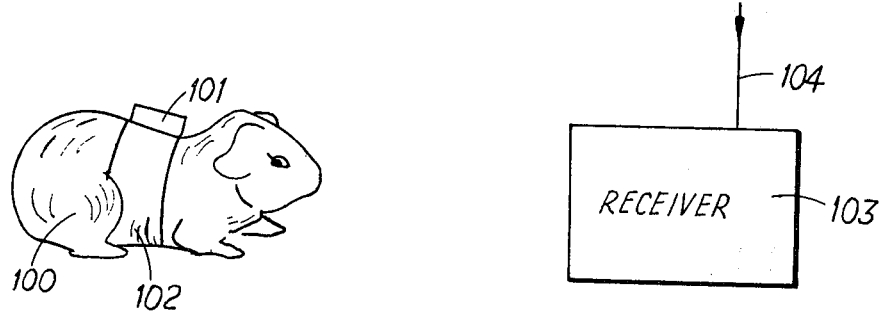

According to another aspect of the present invention there is provided a measuring system comprising a signal processor including storage means for storing a representative of the instantaneous value of a parameter being measured, comparison means for comparing the stored signal, which serves as a reference signal, with the next following signal representative of the instantaneous value of said parameter, means for determining whether the instantaneous value of said parameter is within a predetermined limit of the preceding signal, means for passing to an output only those signals which are within said predetermined limit of the preceding signal, and means for up-dating said storage means by entering said next following signal into the storage means, which signal acts as the next reference signal. The present invention will now be described, by way of example, with reference to the accompanying drawings, in which:

FIG. 1 represents a schematic circuit diagram of a crystal controlled transmitter which is linked with a circuit for measuring temperature, FIG. 2 represents a block schematic circuit of a receiving system for use with the transmitter of FIG. 1, FIG. 3 is a block schematic drawing of the signal processor of FIG. 2, FIG. 3A is a pulse sequence diagram for assisting in the understanding of the transfer, load and reset sequence in FIG. 3, FIG. 4 is a schematic diagram of a converter which is coupled to the output of the signal processor shown in greater detail in FIG. 3, and FIG. 5 illustrates schematically a telemetry system comprising a radio transmitter including a transducer strapped to the back of a guinea-pig and radio receiver for receiving and demodulating the transmitted signal.

Referring to FIG. 1 of the drawings, the circuit may conveniently be regarded as comprising two parts, a temperature sensing part which incorporates a thermistor 10 and a crystal controlled transmitter part which comprises a crystal 11, NPN transistor 12, and an inductance 13.

The temperature sensing part of FIG. 1 comprises an astable or free-running multivibrator comprising PNP transistor 15 and NPN transistor 16. The emitter of the transistor 15 is connected to a positive supply rail 17 and its collector is connected via a resistor 19 to a negative supply rail 20. A diode 18 may be connected optionally in series with the collector of the transistor 15 and the resistor 19. The emitter of the transistor 16 is connected to the rail 20 and its collector is connected through a resistor 21 to the supply rail 17. The collector of the transistor 16 is also coupled to the base of the transistor 15 via a resistor 22 and the capacitor 23 connected in parallel. The base of the transistor 16 is connected by the thermistor 10 to the supply rail 17 and by the capacitor 25 to the junction of the cathode of the diode 18 and one end of the resistor 19.

The time constants of the astable multivibrator circuit are formed on the one hand by the resistance of the thermistor 10, the value of capacitance of the capacitor 25 and the value of the resistor 19, and on the other hand by the forward resistance of the transistors 15 and 16, the diode 18, if connected, together with the value of the capacitor 25. The effect of having two different time constants is as follows: in one condition of the circuit when both the transistors 15, 16 are conductive then the time constant established by the forward resistances of the transistors 15, 16 and the diode 18 together with the capacitance of the capacitor 25 is relatively short and is of the order of 12 milliseconds when the capacitor 25 has a capacitance of $10\mu F$. When the transistors are rendered non-conductive then the capacitor 25 is charged through the thermistor 10 the resistance value of which is temperature dependent. As the thermistor 10 has a negative resistance/temperature characteristic then the time taken to charge the capacitor to a value sufficient to turn the transistors 15 and 16 on is longer at a lower temperature than at a higher temperature. Accordingly, it has been found that the period of time between successive 12 millisecond pulses is inversely proportional to the temperature of the body being measured. The output from the collector of the transistor 15 is coupled to the transmitter circuit from where a signal having a discrete carrier frequency as determined by the crystal 11 is transmitted.

The signal transmitted by the transmitter comprises a short pulse of radio frequency in the frequency band 28 to 28.5 MHz. The pulse width is about 12 milliseconds and the period between pulses is typically 2 to 3 seconds. The transmitted signal is modulated by the pulse signal having the form as described previously. In view of the fact that the transistors 12, 15 and 16 are non-conductive during a relatively long time, approximately 2 to 3 seconds, and that the capacitor 25 is charged through the thermistor 10, the power consumption of the circuit is very small so that the circuit as a whole can be used with a mercury cell giving it a long battery life since the circuit has a low duty cycle. The diode 18 if connected serves to help stabilise the 12ms pulse against supply voltage variations.

The period between successive 12ms pulses is very nearly inversely proportional to the temperature sensed by the thermistor 10.

FIG. 2 shows an illustration of a receiving system for use with a plurality of transmitters, for example ten transmitters, of the type shown in FIG. 1, but with each transmitter having its own unique frequency. The receiving system comprises a channel selector 30, which may be manually or automatically actuated, to scan the transmitters in sequence. The signals emitted by the channel selector 30 instruct the various parts of the receiving system which transmitter is being interrogated. When a particular channel is selected then the channel selector causes a synthesised VFO 31 to generate a signal for use in demodulating the pulse-like signal received by a superhet receiver 32 thereby deriving at the output of the receiver the original pulse transmitted by the transmitter. The pulse is directed to a pulse width discriminator circuit 33 which is so designed as to accept pulses of approximately the correct width. In this way most of any electrical interference may be eliminated. Conveniently the pulse width discriminator 33 may comprise two counters, each having a different maximum count so that the difference between the two counts represents a window. When a pulse is applied to the discriminator both the counters are indexed incrementally for example one pulse per 1 millisecond of the input signal, and for example, if one counter has a maximum count of 10 and the other a maximum count of 16, then for a 12 millisecond pulse this will fall within the above-mentioned window.

As a result of a pulse being received having a width which corresponds to that regarded as being acceptable by the pulse width discriminator 33 then an output pulse is produced. This output pulse is a standard pulse having a duration of, for example, 100 microseconds. The output pulse is directed to a signal processor 34 which turns the incoming signals into a 10-bit binary number representing the period between successive pulses, in such a way as to virtually eliminate any false measurements of the periods. The binary number from the signal processor 34 is passed, together with channel identification information, to respective inputs 37, 38 of a converter 35. The converter 35 produces an analogue voltage signal which is proportional to the temperature of the transmitter. The converter contains a memory for each transmitter which stores the last measured value of the period between signal pulses. In this way a continuous output of the temperature for each transmitter is obtained and this is updated each time the transmitter is interrogated successfully. When the signal processor 34 has acquired the correct measurement of period for the transmitter being interrogated, a channel acquired signal is sent via a line 36 to the channel selector 30 which then steps onto the next channel to be interrogated. In the event of a channel being found to be temporarily or permanently defective, the signal processor 34 is adapted to index the channel selector 30 forwards if an unacceptable reading is still obtained after the sampling point has been interrogated a predetermined number of times in succession. An alarm device 39 is connected to the channel selector 30 which is actuated in the event of a particular channel appearing to be permanently defective which is indicated by the channel still producing an unacceptable signal after the channel has been sampled a predetermined number of times.

Turning now to FIG. 3 which shows the signal processor 34 in greater detail. The function of this circuit is to measure the period between successive 100µs pulses from the pulse width discriminator in such a way as to virtually eliminate false measurements of period. The main parts of the signal processor comprise a clock pulse generator 40, a first counter 41, which is a straightforward incremental counter and may comprise five integrated circuit units of the type SN 7473N, and a second counter 42 which may comprise three integrated circuit units type SN 74193N and which incorporates a store and which is able to count both up and down. For the sake of the present example both the counters 41, 42 are 10-bit binary counters. The clock pulse generator 40 is programmed by the channel selector 30 (FIG.2) so that it generates clock pulses at a rate for each transmitter and so that for example at a base line temperature of say 95°F produces a period of measurement of 1,000 counts. The output from the clock pulse generator 40 is connected to one input of a NAND gate 43 which has as its other input an output from a D type flip-flop or gated memory 44, for example a Texas Instrument SN7474N, which receives on its clock input the standard 100 microsecond signal from the pulse width discriminator 33 (FIG. 2). At the receipt of a signal from the pulse width discriminator 33, the counter 41 is at zero whereas the counter 42 contains the count previously held in the counter 41. Once the standard 100 microsecond signal has been received the $\overline{Q}$ output of the D type flip-flop 44 renders the NAND gate 43 conductive and clock pulses are fed to the counter 41 and to the "down" input of the counter 42 via a NAND gate 45. As the count in the counter 41 increases, the count in the counter 42 is progressively decreased. In the event of the counter 42 reaching zero whilst the count in the counter 41 is still increasing then another D-type flip-flop 46 changes its state in response to a zero signal being received via the NOR gates 47, 48 and 49, the outputs of which are connected to a NAND gate 50 whose output is inverted by an inverter 51 prior to being applied to the clock input of the D-type flip-flop 46.

By virtue of the change of state of the flip-flop 46, an output is sent to gate on the NAND gate 52 and another signal is sent to turn off the gate 45 so that the clock pulses are then fed via the NAND gate 52 to an "up" input of the counter 42 by which the count in the counter 42 begins to count up. When the next signal is received from the pulse width discriminator 33 (FIG. 2) its leading edge causes the D-type flip-flop 44 to change its state so that the output from the NAND gate 43 is inhibited and the counts in the counters 41, 42 are frozen. The count in the counter 41 will now contain the last measured value of the period and the count in the counter 42 will contain the difference between this and the previously measured value of period.

The trailing edge of the input signal initiates a transfer/load/reset sequence of pulses which is shown in FIG. 3A. The trailing edge of the input pulse is used to trigger a "transfer" monostable circuit 55 which has a positive 300 micro second pulse output appearing at a terminal 56 and a negative pulse output appearing at a terminal 57. The negative transfer pulse is used to sample the output of the counter 42, and if this is within for example three counts of zero, which indicates that the last two period measurements are almost equal, the transfer pulse is passed via a NOR circuit 58 to change the state of a D-type flip-flop 59. This pulse after inversion by an inverter 60 is also passed to an appropriate channel memory in the converter 35 (FIG. 2); this memory includes the NOR gates 61 to 70, the other input to each of which comprises a signal from the channel selector.

In order to understand how the signal processor decides whether or not the counts are within three counts of zero, it should be understood that the least significant bits of the counter 42 are connected to the NOR gate 47 whilst the eight most significant bits are connected in groups of four to the NOR gates 48 and 49. Therefore when a count of three or less is in the counter 42 then there will be either no signal or signals appearing on one or both of the leads connected to the NOR gate 47 whilst there will be no output signals from the counter 42 to the NOR gates 48 and 49. The outputs from the two NOR gates are connected to a NAND gate 80 which has as its third input the output $\overline{Q}$ from a D-type flip-flop 81, which is normally at logical 1. In this condition the NAND gate 80 produces an output signal which is applied to one input of the NOR gate 58 the other input of which is connected to the $\overline{Q}$ output 57 of the transfer monostable circuit 55. As a result the NOR gate produces an output which is applied as a clock input to the D-type flip-flop 59. However, in the event of the counter 42 containing a count corresponding to four or more, then no output will appear at the NOR gate and accordingly, the D-type flip-flop 59 will not receive a clock input.

In the situation where the count in the counter 42 is within three counts of zero, the transfer pulse appearing at the Q output 56 of the monostable circuit 55 is applied as an input to a "load" monostable circuit 85, the positive output Q of which appearing at a terminal 86 is applied to a NAND gate 87, and also the trailing edge of this positive output is applied to a "reset" monostable circuit 88. The NAND gate 87 has a second input connected to the positive or Q output of the D-type flip-flop 59 so that a nagative pulse output appears and acts as a channel acquired output signal and which is transmitted back to the channel selector to index it to interrogate the next transmitter. Prior to this happening however, the negative load pulse appearing at the $\overline{Q}$ output 89 of the "load" monostable circuit 85 is used to load the newly measured value of period from the counter 41 into the counter 42 and also this newly measured value is transferred to the converter 35 (FIG. 2). The output from the reset monostable circuit 88 is used to reset the D-type flip-flops 44,46,59 and 81 and also to clear the counter 41. The D-type flip-flop 44 enables the NAND gate 43 to become conductive so that clock pulses are fed from the clock pulse generator 40 to the counters 41 and 42.

The D-type flip-flop 81 is used to detect when a genuine signal has been missed which will result in the count in the counter 41 exceeding its maximum count. If this occurs the output of the D-type flip-flop 81 prevents the transfer pulse from clocking in any of the data to the memories of the converter 35 (FIG. 2).

In the situation where the count in the counter 42 is not within three counts of zero then although the reading is not registered in the converter 35 (FIG. 2) the count in the counter 41 is transferred into the counter 42 to await the beginning of the next cycle. The importance of having this facility is if one of the sampling points is at a significantly different temperature to the next following one, then inevitably there will be no agreement between the count representative of the preceding sample and the new count. However, on the next following interrogation the count loaded into the counter 42 will be that relating to the first interrogation of the new sample point so that under normal circumstances where successive interrogations follow within a matter of seconds of each other, then the temperature change, if any, will be insignificant.

In the block schematic circuit of FIG. 3 the two input NOR gates may comprise SN7402N, the four input NOR gates SN7425N, the two input NAND gates SN7400, the three input NAND gates SN7410N, the D-type flip-flops SN7474N, the monostable circuits SN74121N, the incremental counter 41-five units type SN7473N strapped together and the up-down counter 42-three SN74193N strapped together.

Turning now to FIG. 4 which shows one of a plurality of circuits which comprise the converter 35 in FIG. 2 and which functions to turn the period measurement between successive signal pulses from the transmitter into an analog voltage representing temperature. The period data from the signal processor i.e. the count from the circuit 41 when accepted, is transmitted to a 10-bit store 90 which also has another input to receive a channel identifying signal from the signal processor via a particular one of the NOR gates 61 to 70. The signal stored in the 10-bit store 90 is used to produce an output which is proportional to the reciprocal of the period between the signal pulses in a converter network 91. The output from the converter is an analog voltage representing temperature. The period data stored in the 10-bit store 90 is updated each time an associated transmitter is successfully interrogated.

It should be understood here that there are as many 10-bit stores 90, converter networks 91 and amplifiers 92 as there are signal channels.

The converter network 91 comprises a resistance network whose value is altered by the 10-bit binary number stored in the store 90 in such a way that the total resistance is proportional to the reciprocal of the binary number:
i.e.
1,000 corresponds to R ohms
500 corresponds to 2R ohms
250 corresponds to 4R ohms By passing a constant current through the resistance network there is produced an output voltage which is proportional to the reciprocal of the period between the signals. Hence the output voltage of the resistance network is proportional to the temperature sensed at an associated transmitter.

In a particular example, in the signal processor 34 the period count for 95°F is standardized at 1,000 for all transmitters. The period count at 105°F will show a small variation from transmitter to transmitter. By connecting the amplifier 92 to the converter network 91 output and connecting a variable feedback resistor 93 between the input and output of the amplifier which variable resistor acts as a sensitivity control, the adjustment obtained by the variable resistor allows for the small variation from transmitter to transmitter to be compensated for and the associated amplifier 92 produces an output proportional to temperature such that, for example 95°F corresponds to 0 volts and 105°F corresponds to 5 volts.

If desired the output from the converter 35, after a channel has been interrogated successfully, may be used to provide a digital read-out or may be recorded on a multichannel recorder such as a magnetic tape or film recorder.

It should be understood that although not shown, the circuits of FIGS. 2 to 4 may include interface circuits and power supplies as required.

FIG. 5 shows schematically how the temperature of a guinea-pig 100 may be continuously and remotely measured whilst permitting the animal to move freely in its cage (not shown). A crystal controlled transmitter 101 of the type shown in FIG. 1 is attached to the back of the guinea-pig 100 by an elastic bandage or surgical tape belt 102. A radio receiver 103 including the elements 31 to 36 shown in FIG. 2, is placed outside the cage at some convenient point. By virtue of a radio link established between the radiation from the coil 13 (FIG. 1) of the transmitter and an aerial 104 of the receiver 103, the temperature of the guinea-pig 100 can be monitored continuously as it rests and moves about its cage. Although guinea-pigs have been specifically mentioned any other suitable warm blooded creatures can be used such as human beings, ferrets and monkeys.

Although the transmitter 101 has been shown for convenience of illustration as a block, it is preferred for the transmitter to be packed in a pliable form so that when fitted it will conform more closely to the shape of the surface to which it has been fitted as compared with a block.

Although the present invention has been specifically described with reference to measuring temperature, it should be understood that the system may be readily adapted for measuring other biological physical variables such as pulse and respiratory rates.

Other applications of the present invention may comprise measuring slowly changing parameters in a hostile environment. The measurements may comprise flow temperatures or measurements of strain as detected by strain gauges.

Finally it should be understood that the list of circuit component types used in FIG. 3 is exemplary because for example a person skilled in the art may readily adapt the circuit to work with negative logic rather than positive logic as described.

We claim:

1. A measuring system comprising a signal processor including a first counter for storing a next following signal representative of the instantaneous value of a parameter being measured, a second counter for storing the previous signal representative of the instantaneous value of said parameter, which serves as a reference signal, comparison means for comparing said reference signal with said next following signal, means for passing to an output the signal held in said first counter whenever it is within a predetermined limit of said reference signal, means for up-dating said second counter by entering said next following signal held in said first counter into said second counter, which signal acts as the next reference signal, and clock pulse generator means for supplying clock pulses to both said counters in response to an input signal to said signal processor.

2. A measuring system as claimed in claim 1, further comprising means for determining when a count in said first counter is within the predetermined limit of the count in said second counter and, if so, to transfer the count in said first counter to an output of said signal processor.

3. A measuring system as claimed in claim 2, wherein said up-dating means includes means for transferring the count recorded in said first counter into said second counter irrespective of whether a signal appears at said output of said signal processor.

4. A measuring system as claimed in claim 3, wherein said means for determining whether the difference between the count in said second counter and the count in said first counter is within a predetermined limit, said means for transferring the count in said first counter to said output of said signal processor and said means for transferring the count recorded in said first counter into said second counter irrespective of whether the signal appears at said output of said signal processor, comprises suitably connected logic means.

5. A measuring system as claimed in claim 4, wherein said logic means comprises NAND and NOR gates, monostable circuits and gated memory circuits.

6. A measuring system as claimed in claim 1, wherein said second counter comprises a store for storing the immediately preceding count held in said first counter and is arranged to subtract the received clock pulses from said stored count.

7. A measuring system as claimed in claim 1, in which said first and second counters are binary counters.

8. A measuring system as claimed in claim 1, further comprising a signal converter coupled to said signal processor for converting an output therefrom into an analogue signal representative of the parameter being measured.

9. A measuring system according to claim 1, further comprising means for storing an output of said signal processor.

* * * * *